United States Patent
Schmidt

(10) Patent No.: US 6,197,081 B1
(45) Date of Patent: Mar. 6, 2001

(54) METHOD FOR BIO-REFINING WASTE ORGANIC MATERIAL TO PRODUCE DENATURED AND STERILE NUTRIENT PRODUCTS

(76) Inventor: Erick Schmidt, 5109-59 Avenue, Ponoka, Alberta (CA), T4J 1G7

( * ) Notice: Subject to any disclaimer, the term of this patent is extended or adjusted under 35 U.S.C. 154(b) by 0 days.

(21) Appl. No.: 09/272,015

(22) Filed: Mar. 18, 1999

Related U.S. Application Data

(60) Provisional application No. 60/078,437, filed on Mar. 18, 1998.

(51) Int. Cl.7 ................... C05F 1/00; C05F 9/00; C05F 11/00; C05F 11/08; C05F 15/00
(52) U.S. Cl. ............... 71/1; 71/11; 71/12; 71/13; 71/15; 71/17; 71/18; 71/19; 71/20; 71/22; 71/23; 588/249; 588/258
(58) Field of Search ................... 71/11, 12, 13, 71/15, 17, 18, 19, 20, 22, 23, 1; 106/708; 210/764; 110/346; 585/240, 242; 422/27, 28, 32, 33; 588/258, 901, 249

(56) References Cited

U.S. PATENT DOCUMENTS

| | | |
|---|---|---|
| 3,385,687 | 5/1968 | Brown . |
| 3,442,637 | 5/1969 | Hudson et al. . |
| 3,533,775 | 10/1970 | Brown . |
| 3,635,409 | 1/1972 | Brewer . |
| 4,201,128 | 5/1980 | Whitehead et al. . |
| 4,271,326 | 6/1981 | Mego . |
| 4,285,719 | 8/1981 | Criss . |
| 4,487,699 | 12/1984 | Long, Jr. . |
| 4,582,612 | 4/1986 | Long, Jr. . |
| 4,586,659 | 5/1986 | Easter . |
| 4,659,464 | 4/1987 | Long, Jr. . |
| 4,695,388 | 9/1987 | Long, Jr. . |
| 4,877,531 | 10/1989 | Burkett . |
| 5,147,563 | 9/1992 | Long, Jr. . |
| 5,250,100 | 10/1993 | Armbristor . |
| 5,422,074 | * 6/1995 | Schmidt ................... 422/28 |
| 5,772,721 | * 6/1998 | Kazemzadeh ............ 71/11 |
| 5,853,450 | * 12/1998 | Burnham et al. ........... 71/9 |

FOREIGN PATENT DOCUMENTS

| | | |
|---|---|---|
| 1029978 | 4/1978 | (CA) . |
| 1147572 | 6/1983 | (CA) . |
| 1161577 | 1/1984 | (CA) . |
| WO 93/08849 | 5/1993 | (WO) . |
| WO 95/29884 | 11/1995 | (WO) . |

\* cited by examiner

Primary Examiner—Steven P. Griffin
Assistant Examiner—Eileen E. Nave
(74) Attorney, Agent, or Firm—Akin, Gump, Strauss, Hauer & Feld, L.L.P.

(57) ABSTRACT

A method for treating infectious organic waste material such as dewatered sewage sludge, mixed organic wastes and animal waste. The method includes mixing the infectious organic waste material with a comminuted organic fibrous material to provide a reaction mixture. An oxidizing agent is an optional additive. The reaction mixture is heated in a hyperbaric reactor vessel at an elevated pressure and temperature for a time sufficient to create saturated steam and to produce a substantially denatured product containing inactivated pathogenic agents. The denatured product is dehydrated to produce a free-flowing solid product that may be used in various agricultural, industrial or commercial applications. Odor is controlled so that malodorous compounds are not released to the atmosphere.

20 Claims, No Drawings

METHOD FOR BIO-REFINING WASTE ORGANIC MATERIAL TO PRODUCE DENATURED AND STERILE NUTRIENT PRODUCTS

CROSS-REFERENCE TO RELATED APPLICATION

This application is entitled to priority pursuant to 35 U.S.C. §119)(e) to U.S. Provisional Patent Application No. 60/078,437, filed Mar. 18, 1998.

FIELD OF THE INVENTION

This invention generally relates to a bio-refining treatment of biological waste materials which denatures pathogenic agents. More particularly, the invention relates to processing of human, animal and plant waste materials, such as food wastes and food processing wastes from household and food services businesses; diseased plants; residual meat and bones from meat and fish packers; livestock, poultry and pet carcasses from farm, feedlots, slaughter houses, and veterinarian clinics; and classified or condemned animal carcasses, body parts, organs and tissues which may be specified by national, regional or community disease and control programs for destruction; animal offal; municipal solid waste containing such waste material; and sewage sludge from wastewater treatment plants; all of which carry or may carry transmittable disease agents infectious to human and animals. This material is processed in combination with organic fibrous material to create and produce sterile, denatured, environmentally safe and value-added plant and animal nutrient products.

BACKGROUND OF THE INVENTION

The problem of treatment and disposal of the municipal organic waste materials, food wastes and animal wastes, such as animal carcasses and road kill, has been a challenge to nations, municipalities and industries since the dawn of civilization. There is a growing critical problem for human health risks due to an increasing variety of communicable diseases and pathogenic agents including fungi, bacteria, viruses and transmittable spongiform encephalopathy (TSE). The recent crisis in Europe relating to TSE diseases such as Mad Cow Disease, has accelerated the need for a benign technology which will inactivate and denature these rogue protons (called prions).

Traditionally, processing of organic waste materials entailed aerobic or anaerobic treatment and/or digestion of the materials, and stabilization of the digested materials. For sewage wastewater, additional steps, such as clarification and stabilization, are required, utilizing settling ponds or tanks, and followed by dewatering in lagoons or with mechanical dewatering systems to yield sewage sludge before final disposal. Incomplete inactivation of pathogenic agents in the organic materials occurred primarily at the thermophilic stage during the digestion process. The conventional waste processing or disposal, however, does not guarantee sterilization of pathogens present in the organic materials, requires enormous land areas for lagoons and settling ponds or for landfills, as well as a period of weeks to months for completion, and presents air and water pollution, nuisance and other problems for the surrounding environment.

A number of other waste treatment methods have been tried over the years with varying degrees of success. They include the following types:

Heat treatment is a process used for disinfection and sterilization of sewage sludge. During heat treatments, enteric viruses in the waste materials are expected to be deactivated at or above 70° C. according to established guidelines of the United States Environmental Protection Agency. The method has been claimed effective in destroying most enteric pathogens in waste materials, especially sewage sludge, over an extended period of time.

Ionizing radiation has also been tried as a method to sterilize sewage sludge. 600–850 keV gamma radiation can be employed at dose levels of 1 Mrad to destroy pathogens present in the sewage sludge. $^{60}$Co and $^{137}$Cs are prime sources of the gamma radiation. A system which uses gamma radiation has been developed by Nordion International of Kanata, Ontario, Canada. This system, however, requires high capital expenditures and, furthermore, alters the physical and chemical properties of the sludge. X-ray and ultraviolet radiation have also been used in efforts to disinfect waste materials, but the results showed that the radiation is effective only for indicator microorganisms, such as coliform, and not effective for most pathogens such as gadia and cholera vibro. These latter agents present greater risk to human health.

Incineration is another organic waste treatment process where temperatures in excess of 1,200° C. are used to completely oxidize the biomass or sludge. If all genetic materials associated with microorganisms are destroyed, the opportunity to recycle sterile organic materials increases the cost-effectiveness of the treatment process. There is, however, still a need to dispose of residues from the incineration operation and incineration facilities are expensive. In addition, air emissions from incineration remain a major environmental concern.

Chemical disinfection is also used in treating liquid wastes. Chlorine compounds, ozone, and other sterilizing substances are used to treat liquid wastes. The chemical treatment may produce residues such as chlorinated hydrocarbons which themselves have to be treated or disposed.

Fumigation using certain toxic gasses is also used to inactivate fingi, bacteria, viruses and other pathogens. While a number of substances have been evaluated for their effectiveness in disinfection or sterilization, application of this technology requires great care to prevent human exposure to the toxic gaseous chemicals through inhalation.

Composting utilizes enhanced aerobic biological activities to stabilize organic wastes. Composting processes may vary with the raw materials and the technologies. There are a variety of composters ranging from composting piles to automated composting chambers. A composting facility may take all types of organics and biomass materials and the operation can be continuous if a plug flow process is designed. It may take from a few days to a few weeks for the compost to mature. Construction costs of a well engineered composting facility can be high and the operation requires a good emission control system to protect the health of the operators.

U.S. Pat. No. 3,385,687 demonstrates composting of comminuted municipal organic wastes in a digester. The nitrogen to carbon ratio in the composted product is at least 1:20. U.S. Pat. No. 3,533,775 discusses use of mixtures of comminuted municipal waste and sewage sludge to make fertilizer. As instructed therein, sewage sludge is mixed with municipal waste to provide a uniform mixture. Thereafter, the mixture of sludge and comminuted waste is aerobically digested. The resulting materials are dried and ground for lawn treatment and other uses. Disposal of sewage sludge by composting the sludge with ammonia is shown in U.S. Pat. No. 3,442,637. Disposal of mixed sewage sludge with shredded municipal waste is shown in U.S. Pat. No. 4,586, 659. The resulting mixture is sent to a composter and treated with aerobic bacteria to yield a product useful as a soil conditioner. Composting is not suitable for processing animal carcasses, as composting does not disinfect or sterilize the pathogenic agents contained in the materials to be processed.

Landfilling and landspreading are common. Disposal of animal by-products, diseased carcasses, hide trims, skulls, and hooves from meat processing plants traditionally has been performed by landfilling. Manure is usually stockpiled and spread over fields. Although these materials may be useful as agriculture fertilizers, stockpiling, landfilling, and landspreading of these materials create human health risks. These include air pollution, and groundwater contamination from runoff and provide the breeding grounds for disease-carrying vectors such as flies. Disposal of animal carcasses or other infectious animal wastes, such as hide trim, rotten eggs and the like which are more likely to contain infectious microorganisms, traditionally entailed landfilling. This method, although being cost effective in some places, suffers the disadvantages of contaminating the environment and putting human health at risk. Landfilling and landspreading are not effective for disinfection or eradication of pathogens contained in municipal organic wastes and animal wastes, sewage sludge and other organic wastes, and require extended time periods and large land areas or lagoons. The products of the prior art treatments are, moreover, malodorous and are not sterile. Sterility is desired because of the typical presence of pathogenic organisms in the materials. The end products need to be sterile before being put on the market.

With the eruption of transmittable spongiform encephalopathy (TSE), particularly bovine spongiform encephalopathy (BSE) and scrapie diseases in Europe, inactivation of pathogenic agents is even more necessary. Animal wastes, such as offal, paunch manure and carcasses, are subject to carrying infectious agents including fungi, bacteria, viruses and prions associated with BSE, TSE, etc. A need therefore exists for methods of processing and/or disposal of municipal organic waste materials, sewage sludge, and animal waste without the disadvantages of the prior art.

The present invention overcomes all the disadvantages and problems of the prior art by efficiently treating and processing the various kinds of organic waste products discussed above, in combination with a fibrous material, which fibrous material may be, but need not be obtained from municipal solid organic waste, which is also becoming an environmental burden as landfills are reaching their capacities and waste production is increasing. The present invention involves refining and denaturing the infectious organic waste material and using organic fibrous materials such as newspapers, corrugated cardboard, or even waste organic fibrous material such as mixed waste packaging material, or dried plant products. The inventive bio-refining method for treating a wide variety of waste materials produces sterile, inactive or denatured and environmentally-friendly end products, such as soil conditioners or fertilizers or other useful materials. The invention utilizes saturated steam at elevated temperature and pressure during the denaturing and sterilization process to denature all potential pathogenic agents. Malodorous vapors are evacuated from the headspace in the treatment vessel, condensed, and scrubbed, using commercially available wet and dry scrubbers from companies such as American Air Filter, Louisville, Ky., U.S.A. The treatment time necessary to achieve these results is short, being a matter of hours, particularly when compared to prior art technologies employed for waste processing which can take days.

SUMMARY OF THE INVENTION

The invention effectively addresses the problem of treatment and environmentally safe disposal of organic waste material through a bio-refining process which transforms infectious material, such as waste household foods, waste meat and bone residuals from food processing industries, dead and diseased animal carcasses from all sources, dewatered sewage sludge, and fibrous solid organic waste, into denatured, value-added products.

As used herein, the term "infectious organic waste material" means organic waste material which is actually or potentially infectious, in that it actually or potentially includes any type of pathogenic agent that is capable of causing illness or disease in a human or an animal. Thus, the term includes organic waste materials that are expected to be infectious by virtue of some samples having been found to contain pathogens. It is not necessary that the material actually be tested in advance to determine whether or not it is infectious.

As used herein, the term "denature" and its grammatical equivalents, means both to sterilize and to inactivate pathogenic agents such that they are no longer harmful to humans or animals. This term is chosen for use herein as applying to microorganisms, such as fungi, bacteria or other microorganisms capable of metabolism and reproduction on their own; viruses which may be viewed as either extremely simple microorganisms or as extremely complex molecules that typically contain a protein coat surrounding an RNA or DNA core of genetic material but no semipermeable membrane, that are capable of growth and multiplication only in living cells; and also prions, such as TSE, BSE and scrapie, which are proteins, rather than microorganisms, but nonetheless interact with human and animal biochemicals to form a template or pattern which causes illness or disease. Thus, the term "denature" is used herein as a term which encompasses rendering any of these harmful pathogenic agents not harmful according to the method of the present invention, regardless of whether the pathogenic agent is rendered not harmful by sterilization, inactivation or any other technique within the method of the present invention.

The present invention relates to a method for converting infectious organic waste material into a denatured value-added product, comprising (a) comminuting organic fibrous material, (b) mixing the organic fibrous material with infectious organic waste material to form a reaction mixture, (c) heating the reaction mixture in a hyperbaric reactor vessel at an elevated temperature and at a superatmospheric pressure for a time sufficient to create saturated steam and to convert the reaction mixture into a substantially denatured product containing inactivated pathogenic agents, (d) releasing the vapor from the hyperbaric reactor vessel into a condenser, (e) dehydrating the denatured product in the hyperbaric reactor vessel to produce a free-flowing solid product; and (f) discharging the dehydrated product from the hyperbaric reactor vessel.

The dehydrated denatured products produced in the invention can be employed in agricultural, industrial and commercial applications, such as fertilizers, soil conditioners and animal feed ingredients. The denatured vapor can be recovered and condensed into a denatured liquid for use in applications such as crop irrigation or for production of liquid fertilizer.

The invention utilizes existing and proven equipment for the bio-refining and processing system of organic waste materials. The principal components of the system include storage bins, mechanical sizers, a high pressure steam boiler, a high pressure reactor vessel, a condenser, an environmental scrubber, conveyors and a pelletizer.

DETAILED DESCRIPTION OF THE INVENTION

In general, this invention relates to the treatment of infectious organic waste material, including human, animal and plant waste materials, such as food wastes and food processing wastes from household and food services businesses; diseased plants, such as those affected by fungal diseases; residual meat and bones from meat and fish packers; livestock, poultry and pet carcasses from farm, feedlots, slaughter houses, and veterinarian clinics; and classified or condemned animal carcasses, body parts, organs and tissues which may be specified by national, regional or community disease and control programs for destruction; animal offal; and municipal solid waste containing such waste; and sewage sludge from wastewater treatment plants. The treatment of this infectious material according to this invention denatures the material, rendering it non-infectious.

A reaction mixture is prepared, including infectious organic waste material and the comminuted organic fibrous material which may be derived from the organic fibrous portion of municipal waste, and optionally, an oxidizing agent. The reaction mixture is treated in saturated steam under superatmospheric pressure at elevated temperature to yield denatured and value-added granular end products.

While any type of infectious organic waste material may be treated using this invention, it is particularly effective for treating animal waste which include lipids in amounts on the order of up to about 30 wt %. Such animal waste is difficult to treat because the lipids create a sticky mass that resists effective and efficient treatment and handling.

Animal carcasses, body parts, organs or tissues which may be treated according to the present invention include those of typical livestock including cattle, sheep, goats, hogs, horses, and poultry including chickens, geese, and ducks, and virtually any other animal from any sources whose carcass, body parts, organs or tissues must be disposed. Small complete carcasses or comminuted large carcasses are mixed with organic fibrous material and heated in saturated steam at elevated temperatures and superatmospheric pressures for a time sufficient to provide denatured end products. The large carcasses must be comminuted or shredded to particle sizes with a mean maximum dimension of about 50 mm. The sizing may be done using any suitable equipment, such as hammer mills or shear shredders. Sizing should be done in an enclosed environment to avoid aerosol pathogen emissions into the outside environment. Any odors or aerosol pathogens may be treated using an air filtering system, such as those manufactured by Durr Industrial Products, Inc., Plymouth, Mich., U.S.A., or American Air Filter.

The invention is for denaturing infectious organic wastes containing solid and liquid components, but, excluding plastics, rubbers, metallic materials, glass, concrete and other durable materials. Thus, the invention is primarily for denaturing infectious animal wastes and, secondarily, infectious plant and other wastes as noted above.

Raw or dewatered sewage sludge which can be processed in accordance with the invention typically, but not exclusively, has about 2 wt % to about 25 wt % solids and about 75 wt % to about 98 wt % water, preferably above 3 wt % solids. The sludge with low solids content is initially dewatered using a commercially available filter press such as that sold by Micronics, Inc., Portsmouth, N.H., U.S.A. Dewatering of sewage sludge in the filter press can be employed to increase the solids content of the sludge at least to about 10 wt %, and preferably to at least about 25 wt %. It is preferable to treat dewatered sludge in the reactor, since less water needs to be heated or evaporated, salts present in the sludge dissolved in the water are reduced in the final product, and the time required to denature and dehydrate the sludge is reduced.

The fibrous organic material used in the method of the present invention is needed to make a denatured product that is a free-flowing solid product that can be removed readily from the reactor vessel by using an auger, for example. The organic fibrous material useful in the invention is cellulose-containing material and lignin-containing material which has a moisture content not exceeding about 40 wt %. Thus, the organic fibrous material is sufficiently dry to absorb the water and other liquid components, such as blood, of the infectious organic waste material being treated, as well as the lipid components of the infectious organic waste material, including fat and other types of lipids. Without the use of a suitably dry fibrous organic material to absorb the liquid and lipid components of the infectious organic waste material, it would not be possible to produce the denatured, value-added product as a free-flowing solid product, as desired according to the present invention. The organic fibrous material used in the present invention may be a relatively pure material purchased or otherwise acquired for use in the present invention as described above. However, if desired, the organic fibrous material may include or be derived from organic fibrous waste material, such as municipal waste. The organic fibrous portion of municipal waste useful in the invention includes cellulose and lignin waste materials, for example, newspapers, corrugated board, mixed waste packaging material, and other organic fibrous material. Other organic fibrous material useful in the present invention includes, for example, hay, straw such as oat straw or wheat straw, corn husks, and moss, so long as these materials do not exceed the indicated maximum moisture content. Combinations of the different types of organic fibrous materials can be used in the present invention.

The dry fibrous material is comminuted to a size having a mean maximum dimension of about 1 mm which can be used as filtering and retention media. Well-known devices such as hammer mills and granulators may be employed to comminute the fibrous material. The comminution increases the surface area of the fibrous organic material making it better able to absorb the liquid and lipid components of the infectious organic waste material. The comminuted organic fibrous material should have a maximum moisture content not exceeding 40 wt %, and preferably contains no more than about 25 wt % water, and even more preferably, no more than about 15 wt % water.

The reaction mixture comprising the infectious organic waste material and comminuted organic fibrous material optionally may include an oxidizing agent. The oxidizing agent enhances denaturing of the infectious organic waste material. Preferably, the oxidizing agent used in the present invention contains or adds to the desired product some nutrient value. Preferred are oxidizing agents having anions of nitrate, sulfate or phosphate, or mixtures thereof. The cations for oxidizing agents having such anions preferably are ammonium, sodium, potassium or mixtures thereof.

Oxidizing agents useful for treating the infectious wastes are water soluble, have high oxidizing potential, and are stable under the conditions employed to treat the reaction mixture. Preferred examples of oxidizing agents include ammonium nitrate and potassium nitrate. Examples of other oxidizing agents include, but are not limited to, sulfates such as ammonium sulfate and potassium sulfate, nitric acid and sulfuric acid. Ammonium nitrate is presently the more preferred oxidizing agent and ammonium nitrate in the form of chemical fertilizer rated at 34-0-0 ($N$—$P_2O_5$—$K_2O$) is an especially useful source. Ammonium nitrate should not be used, however, if the end product is used as animal foodstuff.

Generally, when preparing reaction mixtures for treatment to obtain a denatured end product for use as a soil conditioner or plant nutrient, the oxidizing agent is added to the infectious waste organic material in an amount sufficient to significantly enhance the destruction of pathogens, or to enhance the product to a specific nutrient level. An oxidizing agent is expected to accelerate the cleavage of bonds in the organic compounds, particularly those of long chain substances. The amount of oxidizing agent may vary, depending upon the type of oxidizing agent chosen and the nature and type of infectious organic waste material being treated. In general, it is preferred that the oxidizing agent is added to the infectious organic waste material in an amount to provide a weight ratio of oxidizing agent to infectious organic waste material of about 1:30 to about 1:10. This weight ratio works well when the oxidizing agent is ammonium nitrate and when the infectious organic waste material is dewatered sewage sludge or animal waste of the type discussed above, for example. Also as noted above, ammonium nitrate should not be used if the final denatured product produced by the method of this invention is to be used as an animal feed. Thus, typically, but not exclusively, the waste material treated using ammonium nitrate as the oxidizing agent would be used as a soil conditioner or fertilizer, or other such agricultural product.

The infectious organic waste material, with or without an optional oxidizer, together with the comminuted organic fibrous material, provides a reaction mixture. The order of addition of the starting materials does not matter. If an optional oxidizing agent is used, it is preferred, but not essential, to mix the oxidizing agent and infectious organic waste material before combining that mixture with the comminuted fibrous material or before adding comminuted fibrous material to that mixture. Additionally, the materials may be mixed in advance and then charged into a hyperbaric reactor vessel, or the starting materials may be added as separate ingredients into the hyperbaric reactor vessel, as long as the reactor vessel includes agitating or mixing elements, such as a shaft with extended agitator paddles so that the reaction mixture can be mixed within the reactor vessel.

The reaction mixture typically has a weight ratio of infectious organic waste material to comminuted organic fibrous material of about 1:4 to about to 4:1, and preferably about 1:3 to about 3:1. The proportions of infectious organic waste material and comminuted fibrous organic material in the reaction mixture can vary according to the use of the denatured end-product. For example, when the denatured product is intended for use as a fertilizer, the weight ratio of infectious organic waste material to comminuted fibrous organic material may be about 4:1. Where the denatured end-product is intended for use as soil conditioner, the weight ratio of the preferably nutrient-enriched infectious organic waste material to comminuted fibrous organic material may be about 1:3. In the case where the denatured end-product is intended for animal foodstuffs, the weight ratio of animal waste, such as animal carcasses, to comminuted fibrous organic material may be from about 3:1 to about 1:1 to ensure the absorption of lipids, and especially the fatty materials by the fibrous organic material. Those skilled in the art, in view of this disclosure, will be able to determine other useful ratios of the infectious organic waste material to the comminuted fibrous organic material to provide denatured products useful in other specific applications.

After the reaction mixture is in the hyperbaric reactor vessel, the vessel is completely sealed, and then it is heated to about 180° C. to about 200° C., preferably about 180° C. to about 190° C., and more preferably, about 185° C. Due to the aqueous nature of the reaction mixture, saturated steam is generated in the reactor vessel at a pressure of about 140 to about 200 psi (about 9.85 to about 14.06 kg /$cm^2$), preferably about 150 psi (10.55 kg/$cm^2$). If desired, steam from an external source, such as a boiler or other steam-generating equipment, can be injected into the interior of the reactor vessel to accelerate heating and pressurization within the vessel. Heating of the reaction mixture and its consequential exposure to the saturated steam at elevated pressure is continued for a period sufficient to denature the reaction mixture. Typically, this period is about 20 to about 40 minutes, preferably about 30 minutes, but could be longer, on the order of about 60 minutes, if desired.

The reaction mixture treated in the reactor vessel should be agitated throughout the treatment process by an internally heated paddle agitator installed in the reactor vessel. The agitator aids in providing consistent tumbling and blending of the reaction mixture, as well as preventing pooling of liquid near the bottom of the vessel. The agitator also facilitates uniform exposure of the reaction mixture to the high temperature, high pressure saturated steam, and breaks big pieces of waste material into smaller ones.

After completion of the reaction cycle, the reactor vessel is depressurized, preferably in a rapid time of about five minutes, by opening a valve connecting the reactor vessel to a condenser. During the depressurization step, the initial sudden drop in pressure enhances destruction of the cellular components remaining in the reaction product. The denatured vapor passes through a condenser and is collected as a liquid condensate to ensure that the vapor is not released into the atmosphere. The vapor above the liquid in the condenser can be treated to remove malodorous compounds using appropriate scrubbing equipment, such as that commercially available from American Air Filter and Durr Industries, Inc.

The resulting denatured reaction product is dehydrated to form a free-flowing solid that can be removed easily from the reactor vessel using an auger, for example. Such a product also makes handling, storage and shipment easier and less expensive and gives the final product an enhanced shelf life. While and after the reactor is being depressurized during a typical cycle of about 2 hours to about 4 hours, the reactor vessel and the agitator are heated to accelerate drying and dehydration of the denatured product within the reactor vessel. Also during this dehydration cycle, the vapor is evacuated under a vacuum to the condenser. The vacuum also accelerates drying. When the moisture content of the resulting product is about 10% or less, drying is considered complete.

After its recovery from the reactor, the denatured, dehydrated, comminuted product is transported to a cooling area. The air in the cooling area may be scrubbed to remove malodorous compounds. Appropriate scrubbing equipment is readily available commercially, for example, from American Air Filter and Durr Industries, Inc.

Through flexible process conditions, the invention provides a variety of useful end-products. For example, by extending the reaction time from about 30 minutes to about 60 minutes when treating mixtures of sewage sludge and comminuted cellulosic municipal waste at about 150 psi (10.55 kg/cm$^2$) and about 185° C., significant hydrolysis of the cellulose and hemicellulose in the municipal waste can be achieved. The resulting short chain carbohydrate and reducing sugars increase the value of end products, as these substances improve the availability of nutrient and digestibility of the fibrous substances and make the odor of the product more pleasant. In addition, the process advances hydrolysis of the fibrous material.

Without wishing to be bound by any theory, it is believed that the infectious organic waste material, when mixed with the comminuted organic fibrous material, results in the formation of a thin bio-film containing the microorganisms or other pathogenic agents from the infectious waste on the comminuted fibrous particles. The porosity of the comminuted particles is believed to provide a capillary action by which the fibers absorb free water, trace organic compounds, lipids, and trace elements from the infectious waste material and make the denaturing process more efficient. The physical and chemical processes believed responsible for these reactions are due to the formation or breaking of hydrogen bonds, the formation of complexes and chelating.

In addition to generating denatured products, the invention substantially eliminates unpleasant odors associated with disposal of infectious organic waste material such as sewage sludge and animal waste. Without wishing to be bound by any theory, elimination of these odors is believed to be due to a reduction of the amount of sources of odor production generated from microbial activities, together with production of compounds like those in sugars or molasses that have a more pleasant odor. These compounds having a pleasant odor are believed to form due to the hydrolysis of cellulose, production of reducing sugars, and oxidation of organic compounds. Elimination of unpleasant odors also is aided by scrubbing the vapor of residual gasses containing carbon dioxide, methane, and volatile sulfide and amine compounds. The invention therefore substantially eliminates the emission of malodorous gasses to the environment.

Infectious waste materials, when processed in accordance with the invention are sterile and inactivated. All fungi, virus, bacteria (including spore forming bacteria) and other pathogens are completely inactivated and rendered non-viable and prions are destroyed. Therefore, human and animal health risks and liabilities associated with materials handling, storage or reuse are significantly reduced.

The particular type of equipment used in the present invention is not critical, as long as the equipment is capable of performing the operations indicated on the materials to be treated. Thus, for example, any type of comminution device may be used to reduce the materials to be treated to the appropriate particle sizes as discussed above. Moreover, the hyperbaric reactor vessel may be of any suitable size and shape as long as the indicated steam pressure and temperature ranges are maintained. The pressurized vessel can be heated in any suitable manner, including electric conductance or inductive heating, heat supplied from fossil fuel burners, externally fitted steam jacket, and the like.

The operation of the invention may be automated. Such automated equipment would include various automatic or remote controlled inlet and discharge ports, heaters, conveyers, condensing units, gas scrubbers, and all associated sensors and control equipment, all of which is preferably computer controlled in a manner similar to that used with many other automated industrial operations. A skilled computer programmer could readily program a digital computer to monitor and substantially control all aspects of the system in the present invention, as long as the appropriate predetermined parameters of the operation are provided to the programmer.

The invention will now be described in detail by reference to the following specific, non-limiting examples. Unless otherwise specified, all percentages are by weight and all temperatures are in degrees Celsius.

In the Examples below, a stainless steel hyberbaric reactor vessel having an internal volume of up to ten cubic meters and capable of withstanding a maximum pressure of 250 (17.58 kg/cm$^2$) psi was employed. The vessel includes a charge port valve for receiving the infectious organic waste material such as animal waste material, the fibrous organic material, the oxidizing agent and other feedstock materials. The reactor vessel includes a heated paddle agitator to enhance mixing and to provide uniform pressure and temperature conditions throughout the volume of the reaction mixture during the processing time. The reactor vessel was heated with an external steam jacket and an inlet was also provided for steam injection into the interior of the vessel. A discharge port valve is provided in the reactor vessel to discharge the denatured product.

EXAMPLE 1

Treatment of Reaction Mixture of Sewage Sludge and Comminuted Cellulosic Municipal Waste In a pilot scale study, about 135 kg of fibrous organic material in the form of municipal cellulosic waste, primarily paper, magazines and cardboard, was pulverized to a mean maximum dimension of less than about 8 mm using a hammer mill. The pulverized cellulosic waste was delivered to the reactor vessel. The pulverized waste has a water absorption capacity of about 400% to about 600%. About 129 kg sewage sludge (about 3% solids), about 36 kg vegetative and food waste and about 5.1 kg of $NH_4NO_3$ were added into the vessel and mixed with the pulverized municipal fibrous waste to provide a reaction mixture. Loading time was about 15 minutes. While the ammonium nitrate was mixed with the sludge before that mixture was conveyed into the reactor vessel, the oxidizing agent could be added after the sludge and organic fibrous materials are added to the reactor vessel, and in some instances, the oxidizing agent may be eliminated (e.g., for animal foodstuff production, ammonium nitrate should not be added). After loading the reaction mixture, the reactor vessel was sealed. The reaction mixture in the vessel was constantly agitated by an internally heated paddle agitator within the reactor vessel.

Agitation or mixing continued throughout the process to ensure complete dispersion and absorption of the liquid and the absence of any pooling of the liquid at the bottom of the vessel.

The loaded reactor vessel was heated with steam jacket coils to 185° C. Steam was then injected into the reactor vessel over a period of a few minutes to achieve a pressure of 150 psi (10.55 $kg/cm^2$) and a temperature of 185° C. inside the vessel. These pressures and temperatures were maintained for 30 minutes. Thereafter, the reactor was depressurized over a period of 5 minutes by opening a depressurization valve. Vapor escaping from the reactor during depressurization was condensed to form a denatured liquid concentrate. The residual vapor in the condenser was passed through an environmental scrubber before being released into the atmosphere. The condensate was returned to the headwork or the primary settling tank of the sewage treatment system which was used to advantage by raising the temperature of the wastewater and thus increasing microbial activity in the settling pond.

After depressurization, the denatured particulate end product was dehydrated in the reactor vessel heated by the external steam-heated coils and the heated paddle to a moisture content of about 10 wt %, over the course of about 4 hours. The denatured particulate material was cooled and conveyed from the vessel's discharge port. The unloading process took about 20 minutes.

EXAMPLE 2

Test of Effectiveness Against Pathogens

To gauge the extent and the efficiency of the sterilization which can be achieved by the present invention, the mixture was spiked with some typical enteric pathogens. These included *Escherichia coli, Enterococcus faecalis, Aspergillus niger*, Polio virus type 3, *Pseudomonas aeruginosa* and *Bacillus stearothermophilus*. After spiking, the Heterotrophic Plate Count (HPC) was found to be more than $1.9 \times 10^9$ cfu per 100 g in the untreated mixture of sewage sludge, comminuted cellulosic municipal wastes, and ammonium nitrate in similar proportions to Example 1. The mixture was then treated as described in Example 1 above. The results taken at the end of the 30-minute treatment cycle are shown in Table 1. The tests were carried out following the recognized standard. "Diagnostic Procedure for Viral, Rickettsial and Chlamydial Infections," *American Public Health Association*—5th Edition, Eds. Edwin Lennette and Nathalia Schmidt, American Public Health Association, Washington, D.C. (1979).

TABLE 1

Pathogens in untreated and treated waste mixtures and in treated condensate

| Pathogens | Untreated Mixture | Treated Mixture | Treated Condensate*** |
|---|---|---|---|
| Routine samples, average results of 30 samples (90 tests) | | | |
| Total coliforms | >230 per 100 g | <11 per 100 g | <1.1 per 100 ml |
| Faecal coliforms | >230 per 100 g | <11 per 100 g | <1.1 per 100 ml |
| HPC* | $1.3 \times 10^7$ per g | <100 per g | 38 per ml |
| ASB** | >230 per 100 g | <11 per 100 g | <1.1 per 100 ml |
| Spiked with *E. coli.* suspension, average results of 18 samples (54 tests) | | | |
| E. coli | >16,000 per 100 g | <11 per 100 g | <1.1 per 100 ml |
| HPC | $1.9 \times 10^7$ per g | <100 per g | <10 per ml |
| Spiked with *E. faecalis.* suspension, average results of 12 samples (36 tests) | | | |
| E. faecalis | >16,000 per 100 g | <11 per 100 g | <1.1 per 100 ml |
| HPC | $1.3 \times 10^7$ per g | <100 per g | <10 per ml |
| Spiked with Polio virus suspension, average results of 2 samples (6 tests) | | | |
| Polio virus type 3 | isolated | isolated | isolated |
| Spiked with *Ps. aeruginosa* suspension, average results of 6 samples (18 tests) | | | |
| Ps. aeruginosa | >16,000 per 100 g | <11 per 100 g | <1.1 per 100 ml |
| HPC | $3.0 \times 10^7$ per g | <100 per g | $3.8 \times 10^3$ per ml |
| Spiked with *B. stearothermophilus* suspension, average results of 6 samples (18 tests) | | | |
| B. stearothermophilus | >9,000 per 100 g | <11 per 100 g | <1.1 per 100 ml |
| HPC | $4.6 \times 10^6$ per g | <100 per g | 100 per ml |
| Spiked with *A. niger* suspension, average results of 12 samples (36 tests) | | | |
| A. niger | isolated | not isolated | not isolated |
| HPC | $5.6 \times 10^7$ per g | <100 per g | 140 per ml |

*Heterotrophic plate count;
**Aerobic spore-bearing bacilli;
***with regard to the HPC result on the condensate samples, the sampling site for taking the condensate samples was a plastic hose outside the building and was likely in contact with outside contamination, or had a build up of microorganisms in the pump. The 10-minute flushing may, therefore, have been insufficient. When taking this type of sample for testing, the risk of outside contamination is always a concern. As no other type of contamination was detected in these samples, i.e., coliforms, it would appear that the sampling procedure may have been the cause of the low counts detected in a few of the condensate samples, rather than the inadequate treatment by the bioreactor.

As noted in the results of Table 1, the amounts of the tested pathogens contained in the treated particulate end product and the liquid condensate were either below the detection limits for the methods employed or substantially reduced compared to the amounts of such pathogens for the untreated mixture. This shows that the invention is highly effective for destroying the tested pathogens.

EXAMPLE 3

Selected Gas Analysis

As previously indicated, the present invention effectively eliminated unpleasant odors associated with sewage sludge and commingled solid organic waste materials. Odor removal is attributed to diminishing the sources of odor production by microbial activities. Moreover, the process produces compounds having relatively pleasant odors, such as those sugars or molasses produced as a result of hydrolysis of cellulose, production of reducing sugars and oxidation of the organic compounds. An environmental scrubber helped remove or significantly reduce the levels of carbon dioxide, methane and volatile sulfide and, possibly amine compounds in the vapors.

Residual vapor present in the condenser headspace was passed through an environmental scrubber before being released into the atmosphere. The scrubbed gases contain only trace amounts of methane and sulfide compounds which were slightly above the detection limit and a low level of $CO_2$ as noted in Table 2 below. At these low levels, these gases present no problems for the environment.

TABLE 2

Gas components in head space of the reactor vessel.

| Scrubbing | | $CO_2$ (%) | Methane (ppm) | TSC* (ppm) |
|---|---|---|---|---|
| Test 1 | Before | 10.77 | 40 | 23.6 |
| | After | 2.48 | <30 | 1.2 |
| Test 2 | Before | 10.18 | 30 | 24.9 |
| | After | 1.95 | <30 | 5.3 |
| Test 3 | Before | 20.72 | 10 | 27.9 |
| | After | 4.01 | 25 | 0 |
| Test 4 | Before | 4.22 | 55 | 17.4 |
| | After | 0.72 | 6 | 4.2 |
| Test 5 | Before | 6.95 | 140 | 3.7 |
| | After | 0.68 | 15 | 0 |

*total sulfate compounds

EXAMPLE 4

Analysis of Particulate End Product for Certain Land Applications

Using the same procedures as in Example 1 and similar proportions of the materials, but without addition of $NH_4NO_3$, the waste materials were transformed into a useful end product. The denatured solid end product is environmentally safe and has a number of uses. The product has a number of uses as a soil additive and plant nutrient. The solid end product, as show in Table 3, has nutrient levels which make it very useful for variety of agricultural applications. This particular end product was made of a mixture of food waste, sewage sludge, and municipal solid wastes including comminuted fibrous organic material. Standard procedures were followed for the analytical work, and the analysis was carried out by certified private laboratories. The product was produced using the pilot plant facility.

TABLE 3

Some nutritional parameters of the end product

| Parameters | Content |
|---|---|
| Total Kjedahl N (%) | 1.54 |
| Nitrate-N (%) | 0.05 |
| Phosphate (P, %) | 0.07 |
| K (%) | 0.15 |
| S (%) | 0.07 |
| Ca (%) | 1.09 |
| Mg (%) | 0.05 |
| Cu ($\mu$g/g) | 20.1 |
| Fe ($\mu$g/g) | 4240 |
| Mn ($\mu$g/g) | 63.4 |
| Zn ($\mu$g/g) | 38.0 |
| B ($\mu$g/g) | 4.22 |

EXAMPLE 5

Processing of Chicken Carcasses

About 3.2 kg of whole chicken carcasses, 0.3 kg of pulverized phone books and cardboard, and 1.5 kg of alfalfa meal pellets were placed into a sealed bench reactor vessel, similar to the pilot facility except that the size was smaller and that the boiler and reaction chamber were combined. The vessel was externally heated to a temperature of 185° C. at a pressure of 150 psi (10.55 kg/cm$^2$) and the temperature and pressure were maintained for a period of 30 minutes while the reacting materials were under constant agitation.

The vessel was then depressurized as in Example 1. The resulting solid product was dehydrated for a period of about 2 hours to yield a solid denatured product having a moisture content of less than 10%.

This denatured product has value as an animal feed product as reflected in the nutritional values shown in Table 4.

TABLE 4

Nutritional values of the product from Example 5

| Parameters | Contents |
|---|---|
| Fat (%) | 11.8 |
| Crude Fibre (%) | 21.6 |
| Nitrogen (%) | 5.2 |
| Tryptophan (g/kg) | 5.5 |
| Total Volatile Nitrogen (%) | 0.2 |
| Potassium (K) (g/kg) | 14.4 |
| Phosphorus (P) (%) | 0.4 |
| Calcium (Ca) (g/kg) | 17.2 |
| Magnesium (Mg) (g/kg) | 1.82 |
| Amino Acids (%) | |
| Alanine | 1.80 |
| Arginine | 1.83 |
| Aspartic Acid | 2.85 |
| Crystine | 0.13 |
| Glutamic Acid | 3.24 |
| Glycine | 1.80 |
| Histidine | 0.81 |
| Isoleucine | 4.43 |
| Leucine | 2.10 |
| Lysine | 5.01 |
| Methionine | 0.38 |
| Phenylalanine | 1.10 |
| Proline | 1.80 |
| Serine | 1.09 |
| Threonine | 1.07 |
| Tryptophan | 0.55 |

TABLE 4-continued

Nutritional values of the product from Example 5

| Parameters | Contents |
|---|---|
| Tryrosine | 0.75 |
| Valine | 1.52 |

These nutritional values suggest that the product can be used as foodstuff or feed supplement for poultry and/or livestock as it can supply these animals with sufficient energy (fat), amino acids and high fibers of various forms.

EXAMPLE 6

Processing Livestock Carcasses and Mixed Organic Wastes

Using the pilot plant facility, the present invention was used to process animal carcasses and mixed organic wastes. In a typical trial, the input materials have the following compositions:

| | |
|---|---|
| pulverized waste paper | 3 kg |
| cardboard | 3 kg |
| swine rib bones | 8 kg |
| grass clippings | 4 kg |
| porcupine carcass | 4 kg |
| sheep skulls | 34 kg |
| sheep organs | 18 kg |
| restaurant food wastes | 14 kg |
| alfalfa stems | 6 kg |

These materials were placed into the reactor vessel employed in Example 1. The vessel was then sealed and heated by steam to a temperature of 185° C. at a pressure of 150 psi (10.55 kg/cm$^2$). These conditions were maintained for a period of 30 minutes while the materials in the vessel were under constant agitation. The vessel then was depressurized as in Example 1. The resulting denatured solid products were found to have excellent properties for animal feed and/or supplement.

The present invention provides distinct advantages over prior art treatments of animal wastes and municipal solid wastes and dewatered sewage sludge. All of the reaction products were denatured by saturated steam at high temperature and pressure. Pathogenic agents with infectious diseases were effectively denatured through oxidation and hydrolysis under the various reaction conditions.

Unpleasant odors were reduced by the method of the present invention, by enclosing the system, and by using odor control devices. Operators have no direct exposure to the materials once they are delivered to the reactor vessel. The comminuted or pulverized fibers act as an absorbent for retention of free water, and act as an absorbent for organic compounds, including blood and lipids such as animal fat which adversely affects other treatment systems, and trace metals.

The particulate matter and condensate were denatured to the extent that all fungi, bacteria (including spore-forming bacteria), viruses and other pathogenic agents were completely inactivated and rendered non-viable during denaturing. Therefore, human health risks and liabilities associated with handling, storing or recycling materials containing pathogens were significantly reduced.

In addition to treating the primary infectious organic waste material, by recycling and treating the fibrous organic materials from municipal solid waste, the volume of the municipal solid wastes can be significantly reduced. It is estimated that municipal solid wastes contain at least 40% recyclable organic fibrous materials and degradable organic substances. These can be used or processed in the present invention and help relieve the burden on landfills.

It is believed that the method of the present invention stimulates the hydrolysis of cellulose materials and produces short chain substances which can be more readily digested by microorganisms. Hydrolysis occurs in the vessel as a result of the comminution of the fibrous organic material into small pieces and subjecting them to high pressure and temperatures and active radicals. The presence of oxidants, such as ammonium nitrate, accelerates the hydrolysis and oxidation process. The process is aided by the formation of free protons and/or radicals during the dissolution of the oxidant, such as ammonium nitrate.

The method of the present invention provides a significant savings of time and space compared to prior art processes. The entire treatment process, from delivery of raw materials to the reactor vessel, through to and including the dehydration and pelleting operations requires about 5 hours. This means that the whole process may be accomplished in one working shift. Since the treatment time is short, large land areas are not required as in the prior art (e.g., composting), and treatment times are reduced from weeks and months, to a few hours. Overall, the present invention provides a very safe, efficient, effective system for treating infectious organic waste material.

It will be appreciated by those skilled in the art that changes could be made to the embodiments described above without departing from the broad invention concept therein. It is understood, therefore, that this invention is not limited to the particular embodiments disclosed, but it is intended to cover modifications within the spirit and scope of the present invention as defined by the appended claims.

What is claimed is:

1. A method for converting infectious organic waste material selected from the group consisting of food waste, food processing waste, animal carcasses, animal body parts, animal organs, animal tissues, and mixtures thereof, into a denatured, value-added solid, plant or animal nutrient product, wherein the infectious organic waste material contains solid and liquid components, the method comprising (a) comminuting absorbent organic fibrous material from a source other than the infectious organic waste material;

(b) mixing the absorbent organic fibrous material with the infectious organic waste material to form a reaction mixture;

(c) heating the reaction mixture in a hyperbaric reactor vessel at an elevated temperature and at a superatmospheric pressure for a time sufficient to create saturated steam, to hydrolyze the absorbent organic fibrous material and to convert the reaction mixture into a substantially denatured plant or animal nutrient product containing inactivated pathogenic agents;

(d) releasing vapor from the hyperbaric reactor vessel into a condenser;

(e) dehydrating the denatured plant or animal nutrient product in the hyperbaric reactor vessel to produce a free-flowing solid denatured plant or animal nutrient product; and (f) discharging the dehydrated free-flowing solid denatured plant or animal nutrient product from the hyperbaric reactor vessel.

2. The method of claim 1 wherein the absorbent organic fibrous material is selected from the group consisting of cellulose-containing material and lignin-containing material not exceeding about 40 wt % moisture content.

3. The method of claim 2 wherein the absorbent organic fibrous material is selected from the group consisting of newspaper, cardboard, cellulosic packaging materials, straw, hay, moss and mixtures thereof.

4. The method of claim 1 wherein the absorbent organic fibrous material is present in the reaction mixture in an amount sufficient to provide a weight ratio of the absorbent organic fibrous material to the infectious organic waste material of about 1:4 to about 4:1.

5. The method of claim 4 wherein the weight ratio is about 1:3 to about 3:1.

6. The method of claim 1 further comprising mixing an oxidizing agent with the reaction mixture.

7. The method of claim 6 wherein the oxidizing agent is an oxidizing agent containing nutrient value.

8. The method of claim 7 wherein the oxidizing agent contains an anion selected from the group consisting of a nitrate, a sulfate, a phosphate and mixtures thereof.

9. The method of claim 6 wherein the oxidizing agent is ammonium nitrate, and the free-flowing solid denatured nutrient product is a plant nutrient.

10. The method of claim 9 wherein the ammonium nitrate and the infectious organic waste material are present in the reaction mixture in a weight ratio of ammonium nitrate to infectious organic waste material of about 1:30 to about 1:10.

11. The method of claim 1 wherein the elevated temperature of step (c) is about 180° C. to about 200° C., and the superatmospheric pressure is about 140 psi (9.85 kg/cm$^2$) to about 200 psi (14.06 kg/cm$^2$).

12. The method of claim 11 wherein the reaction mixture is maintained at the elevated temperature and the superatmospheric pressure for about 20 minutes to about 40 minutes.

13. The method of claim 11 wherein the elevated temperature is about 185° C. and the superatmospheric pressure is about 150 psi (10.55 kg/cm$^2$).

14. The method of claim 13 wherein the reaction mixture is maintained at the elevated temperature and the superatmospheric pressure for about 30 minutes.

15. The method of claim 1 further comprising agitating the reaction mixture during steps (b), (c) and (e).

16. The method of claim 1 wherein step (e) comprises dehydrating the denatured product to a moisture content of not greater than about 10 wt %.

17. The method of claim 1 wherein step (c) further comprises initially injecting steam into the reactor vessel.

18. The method of claim 1 further comprising scrubbing the vapor to remove malodorous compounds from the vapor.

19. The method of claim 1 wherein the infectious organic waste material is selected from the group consisting of animal carcasses, animal body parts, animal organs, animal tissue and mixtures thereof, the method further comprising mixing an oxidizing agent with the infectious organic waste material for the production of fertilizer.

20. The method of claim 19 wherein the oxidizing agent is ammonium nitrate and wherein the ammonium nitrate and the infectious organic waste material are present in the reaction mixture in a weight ratio of about 1:30 to about 1:10.

* * * * *